United States Patent [19]

Poshemansky et al.

[11] Patent Number: 4,991,423
[45] Date of Patent: Feb. 12, 1991

[54] METHOD OF GAS-CHROMATOGRAPHIC ANALYSIS OF MIXTURES AND DEVICE THEREFOR

[76] Inventors: Vladimir M. Poshemansky, 2-oi Pavlovsky pereulok, 20, kv. 20; Eduard P. Skornyakov, ulitsa admirala Makarova, 21, kv. 14; Jury K. Fiseisky, ulitsa Alyabieva, 2, kv. 36, all of, Moscow, U.S.S.R.

[21] Appl. No.: 397,738
[22] Filed: Aug. 23, 1989
[51] Int. Cl.$^5$ ............................................. G01N 30/26
[52] U.S. Cl. ..................................................... 73/23.35
[58] Field of Search .................. 73/23.1, 23.35, 23.39, 73/23.41, 23.42

[56] References Cited

U.S. PATENT DOCUMENTS 2,920,478  1/1960  Golay ................................ 73/23.35

FOREIGN PATENT DOCUMENTS

1122965  11/1984  U.S.S.R.

Primary Examiner—Hezron E. Williams
Assistant Examiner—Joseph W. Roskos
Attorney, Agent, or Firm—Burgess, Ryan & Wayne

[57] ABSTRACT

A method of gas-chromatographic analysis of mixtures involves the use of a chromatograph column comprising a capillary tube which continuously passes a carrier-gas flow saturated with solvent vapors at a temperature below the chromatograph column temperature maintained above the solvent vapor condensation point and below the solvent boiling point, a sample of a mixture to be analyzed being periodically supplied to the column after attaining the equality between the quantity of solvent vapors supplied to the column and the quantity of vapors removed therefrom. To this end, the device for accomplishing the proposed method comprises a saturator partially filled with liquid solvent and placed between a carrier-gas source and means for supplying samples of an analyzed mixture of the column, the saturator being enclosed in a thermostat.

7 Claims, 6 Drawing Sheets

FIG.10

METHOD OF GAS-CHROMATOGRAPHIC ANALYSIS OF MIXTURES AND DEVICE THEREFOR

FIELD OF THE INVENTION

The present invention relates to gas chromatography and, in particular, to techniques for gas-chromatographic analysis of mixtures of solutes and to devices therefor.

The invention may be suitable for analyzing intricate multicomponent mixtures of organic compounds in such vital branches of science and engineering as medicine, biology, chemistry, petroleum refining industry, agriculture, food industry, water and air pollution control.

BACKGROUND ART

There is widely known a method of gas-chromatographic analysis of mixtures of solutes involving the use of a capillary chromatographic column, through which a flow of inert carrier gas is continuously passed, and comprising the steps of periodically introducing a sample of a mixture to be analyzed into the chromatograph column and detecting separated components of said analyzed mixture at the column output by the use of a known detector (cf. U.S. Pat. No. 2,920,478).

In the foregoing method, the capillary chromatographic column is a capillary tube of a suitable inert material with an internal diameter of 0.23 to 0.53 mm, its internal surface being coated with a thin layer (0.2 to 1.0 $\mu$) of a nonvolatile (low-volatile) high-molecular weight liquid which is the stationary liquid phase.

With such a method, the chromatographic column has to be replaced each time it is necessary to change selectivity of chromatographic separation in switching to the analysis of a new class of mixtures, say in the event of the change-over from the analysis of nonpolar organic compounds to the analysis of polar compounds. To enable the analysis of a wide range of substances of different polarity, the device for carrying out the foregoing method should comprise several replaceable capillary chromatograph columns filled with different stationary phases. Production of each column entails a complicated process of filling it with a stationary phase, which calls for utilization of special facilities and requires high skill on the part of the operator.

Moreover, it should be borne in mind that the cost of such a column is fairly high: a highly efficient filled capillary chromatographic column costs about a thousand dollars on the world market. Inasmuch as the known device comprises a set of several capillary chromatograph columns with different phases, its cost drastically increases.

With the foregoing method, the change-over to capillary chromatographic columns having a small internal diameter (less than 100 $\mu$) and, accordingly, higher effectiveness (up to 100 thousand theoretical plates per meter) is limited by the production techniques involved. This limitation is due to the fact that, with a smaller internal diameter of the capillary column, increasing difficulties are encountered in uniformly coating the internal surface of such columns with a viscous high-molecular liquid. More specifically, the known techniques for applying the stationary liquid phase make it hard to obtain theoretically predicted highly efficient slot capillary columns by etching rectangular channels in silicon plates.

Furthermore, in the known method the capillary chromatograph columns spontaneously change their separation properties in the course of time. Stability of the separation properties of such capillary columns and their service life are dependent upon many factors, the most important of which are the operating temperature of the column, concentration of oxygen and water vapours in carrier gas, chracteristics of the material of which a particular column is made and composition of an analyzed mixture. It is common knowledge that the presence of a large amount of solvent, particularly water in a sample of a mixture to be analyzed causes rapid elution of the layer of the stationary liquid phase from the first section of the capillary column and, in effect, impairs the separation properties of the column.

In operation according to the above method at high column temperatures required to separate high-boiling organic compounds, the column acts as a source of intricate gas evolution (including residual solvent, monomers for stationary-phase synthesis and products of catalytic thermal breakdown), which increases the detector noise.

When the column is subjected to programmed heating, special techniques are required to suppress said noise in the course of the analysis procedure. Vapors of the stationary phase accumulated in the detector change its operating parameters in the course of time whereby it should be periodically cleaned or replaced. An adverse effect of said gas evolution is particularly strong in the case of a mass-spectrometric detector.

There is also known a method of gas-chromatographic analysis of mixtures with packing chromatograph columns, which comprises the steps of continuously passing a mixture of inert carrier gas and water vapors through the chromatograph column, introducing periodically a sample of a mixture to be analyzed into said column and detecting the separated components of said mixture at the column output (cf. M. S. Vigdergaus et al.: "Gasovaya khromatographiya s neidealnimi eluentami", 1980, Nauka publishers, Moscow, pp 75-99).

With such a method, the chromatograph column is a tube of a suitable inert material filled with particles of a solid carrier (Chromosorb W). The column temperature is maintained below the water-vapor dew point and water condensed on the carrier particles serves as the stationary phase in separating and analyzing polar organic compounds. The foregoing method of gas-chromatographic analysis does not ensure high efficiency in analyzing substances, a disadvantage attributable to the presence of many pores in carrier particles increasing elution of the chromatographic strips.

Moreover, with the known method the packing chromatograph column rapidly changes its separation properties with time due to the fact that water acting as an active solvent elutes the dissolved components of the solid carrier, thereby changing its surface, a factor preventing reproduction of chromatographic analysis data with time.

Other known techniques for gas-chromatographic analysis of mixtures with vapors of various solvents used as a carrier gas relate to a method of gas-solid chromatography, wherein solvent vapors are used to modify the surface of solid adsorbents. The process of modifying the surface of solid adsorbents essentially consists in that the solvent vapor block or deactivate chemical or physical heterogeneity (the so-called "active centres") on the adsorbent surface. This increases the separation efficiency and often reduces the analysis time as compared with methods involving the use of an inert carrier gas. In the aforementioned method, the temperature of the chromatograph column is maintained substantially higher than the boiling point of the solvent used (cf. Journal of Chromatographic Science, Vol. 21, Aug. 1983, Ion F. Parcher "A Review of Vapor Phase Chromatography": Gas Chromatography with Vapor Carrier Gases, pp 346–351).

As is the case with another known method involving the use of packed columns, the foregoing method of gas-solid chromatography is characterized by low separation and a longer analysis time as compared with the prior-art methods of gas-chromatographic analysis, in which highly efficient capillary columns are utilized.

Also known in the art is a method of gas-chromatographic analysis of mixtures with a chromatograph column representing a hollow capillary tube, which comprises the steps of continuously passing through said tube a carrier-gas flow containing solvent vapours, periodically introducing a sample of a mixture to be analyzed mixture into the chromatograph column maintained at a predetermined temperature and detecting at the output of the chromatograph column the components of the analyzed mixture separated in said column (cf. U.S. Pat. No. 1,122,965).

There is known a device for gas-chromatographic analysis of mixtures to accomplish the foregoing method, which comprises components successively interconnected via a pipe-line, more particularly, a carrier-gas source, a means for introducing samples of an analyzed mixture into the chromatograph column representing a hollow capillary tube placed in a thermostat, and a detector, the known device being also provided with a means for supplying solvent vapors to the carrier gas flowing to the chromatograph column (cf. U.S. Pat. No. 1,122,965).

In the afore-mentioned device for accomplishing the known method, said means for supplying solvent vapors to the carrier gas flowing to the chromatograph column comprises a solvent flow booster connected with an evaporator at the input of the capillary chromatograph column and receiving the carrier gas mixed with solvent vapors at the evaporator and supplied to the chromatograph column as a vapor gas mixture. With such a vapor-gas mixture fed to the chromatograph column representing a capillary tube operating in the condensation mode (that is, at the temperature close or equal to the solvent condensation temperature), there occurs gradual growth of the condensed liquid-phase film on the walls of the capillary tube serving as the column whereby its thickness changes. As a result, the separation properties of the column spontaneously change in operation, a disadvantage bringing about unstable analysis conditions in the course of time.

Moreover, at a certain moment the layer of solvent condensed on the inner surface of the capillary tube acting as the column may block the inner section of the tube, thus forming a solvent lock, a disadvantage sharply decreasing separation efficiency and making impossibly a gas-chromatographic analysis.

Due to the above peculiarities characterizing formation of the vapour-gas mixture supplied to the chromatograph column, the foregoing device for accomplishing the known method does not permit changing (increasing) as desired the separation capacity of said column. To this end, it is necessary to replace the chromatographic column with another, say a longer one.

BRIEF DESCRIPTION OF THE INVENTION

It is an object of the present invention to increase stability of analysis conditions with time and effectiveness in separation of components of analyzed mixtures.

Another object of the invention is to ensure a controlled change (increase) in separation properties of a chromatograph column without having to replace it with a new column.

The foregoing object is accomplished by that in a method of gas-chromatographic analysis of mixtures with a chromatograph column representing a hollow capillary tube through which a carrier-gas flow containing solvent vapors is continuously passed, comprising the steps of periodically introducing a sample of a mixture to be analyzed into the chromatograph column maintained at a predetermined temperature and detecting at the output of the chromatograph column components of the analyzed mixture separated in said column, according to the invention, the carrier-gas flow supplied to the chromatograph column is saturated with solvent vapours at a temperature below or equal to the chromatograph column temperature, said chromatograph column temperature being maintained above the solvent vapor condensation point and below the solvent boiling point, while introduction of said sample of the mixture to be analyzed is effected after attaining the equality between the quantity of solvent vapors supplied to the chromatograph column and the quantity of solvent vapors removed therefrom.

It is of advantage that the equality between the quantity of solvent vapors supplied to the chromatograph column and the quantity of solvent vapors removed therefrom should be determined by additionally introducing a sample of mixture to be analyzed into the chromatograph column and noting the moment at which the output of the mixture components from the chromatograph column is stabilized. It is also advantageous that a measured amount of solvent vapors should be additionally supplied to the chromatograph column before periodic introduction of the sample of the mixture to be analyzed into said column.

Preferably additional introduction of the measured amount of solvent vapors into the chromatograph column is repeated many times until a desired degree of separation of the components of the analyzed mixture is obtained.

There is also provided a device for gas-chromatographic analysis of mixtures to accomplish the proposed method, comprising components successively interconnected via a main pipe-line, more particularly, a carrier-gas source, a means for supplying samples of a mixture to be analyzed mixture to the chromatograph column representing a hollow capillary tube placed in a thermostat, and a detector, as well as a means for supplying solvent vapors to the carrier-gas flow fed to the chromatograph column, wherein, according to the invention, said means for supplying solvent vapors to the carrier-gas flow fed to the chromatograph column comprises a main saturator partially filled with liquid solvent and placed on the main pipe-line between the carrier-gas source and said means for introducing samples of the mixture to be analyzed, said saturator being provided with a thermostat for maintaining a predetermined temperature in saturating the carrier gas with solvent vapors.

It is preferable that a thermostat of a main saturator and a thermostat of a chromatograph column are made integral, thereby forming a common thermostat.

It is further preferable that the device for accomplishing the proposed method should comprise an additional pipe-line connecting the carrier-gas source to the input of the detector and to the output of the chromatograph column and components successively arranged on said additional pipe-line, more specifically, a carrier-gas pressure regulator, an additional saturator partially filled with liquid solvent and placed in its thermostat to maintain a predetermined temperature in saturating the carrier gas with solvent vapors, and a fixed pneumonic resistor inserted at the detector input after the point of connection of the additional pipe-line with the detector input and with the output of the chromatograph column.

Such a construction of the device for gas-chromatographic analysis of mixtures to accomplish the proposed method makes it possible to increase effectiveness and separation capacity of the chromatograph column and also stability of separation conditions with time.

BRIEF DESCRIPTION OF DRAWINGS

These and other objects and features of the invention will become apparent from the discussion of specific embodiments thereof, taken in conjunction with the accompanying drawings, wherein.

DETAILED DESCRIPTION OF THE INVENTION

The proposed method of gas-chromatographic analysis of mixtures consists in using a chromatograph column representing a hollow capillary tube maintained at a predetermined temperature and continuously passing a carrier-gas flow saturated with solvent vapors at a temperature below or equal to the chromatograph column temperature. Said chromatograph column temperature is maintained above the solvent vapour condensation point and below the solvent boiling point. Periodic introduction of a sample of a mixture to be analyzed into the column is effected after attaining the equality between the quantity of solvent vapors supplied to the chromatograph column and the quantity of solvent removed therefrom. The components of the analyzed mixture separated in the chromatograph column are detected at the output of said column.

Said equality is checked by additionally introducing samples of a mixture into the capillary tube and noting the moment which the output of components of said mixture from the chromatograph column is stabilized.

Under these conditions, a layer of the stationary phase on the inner surface of the capillary tube acting as the chromatograph column is formed from molecules of solvent vapors adsorbed on the inner surface of the capillary tube before the chromatographic analysis. After a certain time period, equilibrium is reached in the capillary tube, a state characterized by that the quantity of solvent vapors supplied to the capillary tube with the carrier-gas flow equals the quantity of solvent vapors removed from the capillary tube with the carrier-gas flow. Under such conditions, the solvent content may not be gradually increased in the capillary tube and its separation capacity will not change with time.

The separation capacity and effectiveness of such a chromatograph column will remain constant due to continuing renewal of the layer of the stationary phase formed by molecules of solvent vapours adsorbed on the inner surface of the capillary tube. This ensures stable conditions for a chromatographic analysis with time and, according to experimental data, high separation efficiency. A remarkable fact is that the capacity of a stationary-phase layer formed from adsorbed solvent molecules is comparable with the capacity of conventional high-molecular stationary phases widely used at the present time in gas chromatography. This means that the quantity of a mixture of analyzed substances placed in the capillary tube acting as the chromatograph column in the proposed method does not differ from the quantity of samples introduced into conventional chromatograph column. Such a result was absolutely unexpected and could not be predicted on the known theory.

Owing to the afore-mentioned conditions for forming the stationary phase in the capillary tube according to the proposed method, separation selectivity may be changed as desired without replacing the column (merely by changing the solvent).

In another embodiment of the method forming the subject of the present invention, a controlled increase in separation capacity of the capillary tube acting as the chromatograph column may be obtained without column replacements, more specifically, by additionally introducing a measured amount of solvent vapors into the capillary tube after equilibrium has been reached therein.

Additional introduction of a measured amount of solvent vapors into the capillary tube after attaining equilibrium therein may be repeated many times until a desired degree of separation of components of an analyzed mixture is obtained.

Also unexpected was the above feature of the proposed method consisting in the possibility of controlling changes in separation capacity of the column by supplying it additionally with measured amounts of solvent.

In the preferred embodiments of the method forming the subject of the present invention, the analyzed mixture is a mixture of normal spirits $C_1$–$C_5$ or normal spirits $C_1$, $C_3$, $C_4$ and aromatic hydrocarbons, the chromatograph column is a hollow capillary tube of stainless steel, the carrier gas is helium, and the solvent is distilled water. However, the invention may variously otherise embodied by those skilled in the art, who may think of other suitable carrier gases, solvents and mixtures of substances for carrying out a gas-chromatographic analysis.

To accomplish the proposed method, the device for gas-chromatographic analysis of mixtures according to the invention comprises components successively interconnected by means of a pipe-line 1 (FIG. 1), more specifically, a carrier-gas source 2, a carrier-gas pressure regulator 3 with a pressure indicator 4 placed at its output, a capillary tube 5 for carrier-gas preheating, a means (saturator 6) for supplying solvent vapours to a carrier-gas flow fed to a chromatograph column 7 made as a hollow capillary tube, a means 8 for introducing samples of an analyzed mixture into the chromatograph column 7, and a detector 9.

Figure 1:
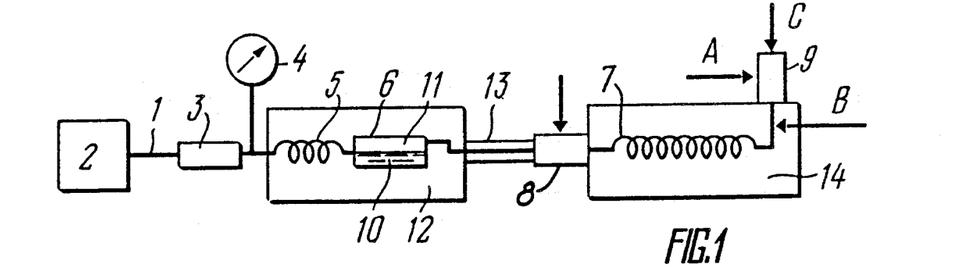
FIG. 1 is a schematic diagram of the device for gas-chromatographic analysis of mixtures to accomplish the method in compliance with the invention.

As stated above, in the preferred embodiment of the device for carrying out the proposed method, the means for supplying solvent vapours to the carrier-gas flow fed to the chromatograph column 7 comprises the saturator 6 partially filled with a liquid solvent 10, for example, a volatile liquid such as distilled water. A portion 11 of the saturator 6 free from the solvent 10 is a vapor space blown with the carrier-gas flow. The saturator 6 includes a thermostat 12 to maintain a predetermined temperature in saturating the carrier gas with the vapors of the solvent 10. The capillary tube 5 is placed in the same thermostat 12.

A heater 13 is used to heat the section of the pipe-line 1 between the thermostat 12 and the means 8 for introducing samples of mixture to be analyzed into the chromatograph column 7. The means 8 is essentially an evaporator used to evaporate a liquid sample of an analyzed mixture. The chromatograph column 7 is a hollow capillary tube enclosed in its thermostat 14 to maintain a predetermined temperature in separating components of the mixture to be analyzed.

The detector 9 is a plasma-ionization detector, in which oxygen and hydrogen are supplied in the direction of arrows A, B and the components to be detected are fed in the direction of arrow C.

Figure 2:
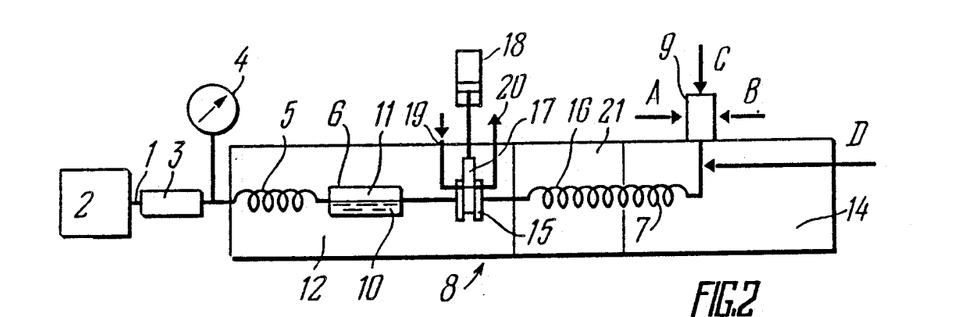
FIG. 2 shows one of the preferred embodiments illustrated in the schematic diagram of FIG. 1, wherein introduction of a sample of a mixture to be analyzed mixture into a chromatograph column is effected from the flow.

The embodiment of the device for carrying out the proposed method illustrated in FIG. 2 is essentially similar to that of FIG. 1.

The difference therebetween is that the means 8 (FIG. 2) for introducing samples of an analyzed mixture comprises the following components arranged on the pipe-line 1: a metering device 15 enclosed in the thermostat 12, and a liquid-phase evaporator formed of a hollow tube 16.

A rod 17 of the metering device 15 is kinematically linked with a drive 18 and has a transverse through hole serving as a proportioner. The sample is taken from the flow of the mixture to be analyzed liquid fed to the metering device 15 through a pipe-line 19 and removed therefrom through a pipe-line 20.

The output of the capillary tube 16 is connected with the input of the chromatograph column 7. The capillary tube 16 is enclosed in its individual thermostat 21 to maintain a temperature equal to the evaporating point of the mixture to be analyzed.

Gas is supplied to the detector 9 in the direction of arrow D.

Figure 3:
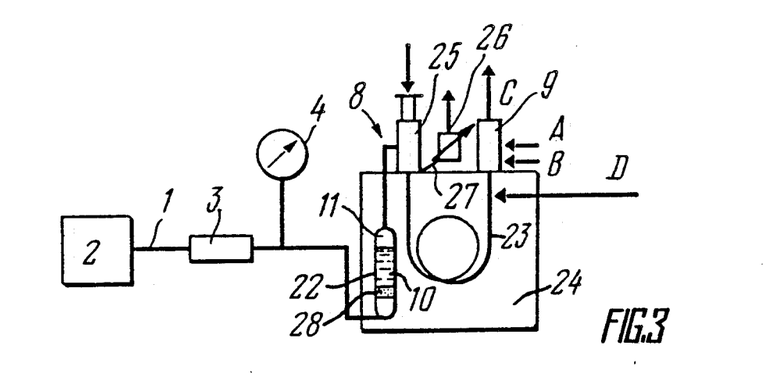
FIG. 3 is a schematic diagram of another embodiment of the proposed device for accomplishing the method in compliance with the invention.

The embodiment of the device for carrying out the proposed method illustrated in FIG. 3 is essentially similar to that of FIG. 1.

The difference therebetween is that the thermostat of a carbonator 22 (FIG. 3) and the thermostat of a chromatograph column 23 are made integral, thus forming a common thermostat 24.

In the illustrated embodiment, the means 8 for introducing samples of a mixture to be analyzed comprises a liquid-sample evaporator 25 and a pneumonic resistor 26, for example, a needle valve disposed on a pipe-line 27 interconnecting the evaporator 25 and the pneumonic resistor 26 and designed to vent a portion of the carrier gas to atmosphere.

The saturator 22 is a cylindrical vessel having in its lower portion a porous partition 28, which is a Schott filter. Placed above the porous partition 28 is a layer of the liquid solvent 10 passing bubbles of the carrier gas saturated with solvent vapors.

Figure 4:
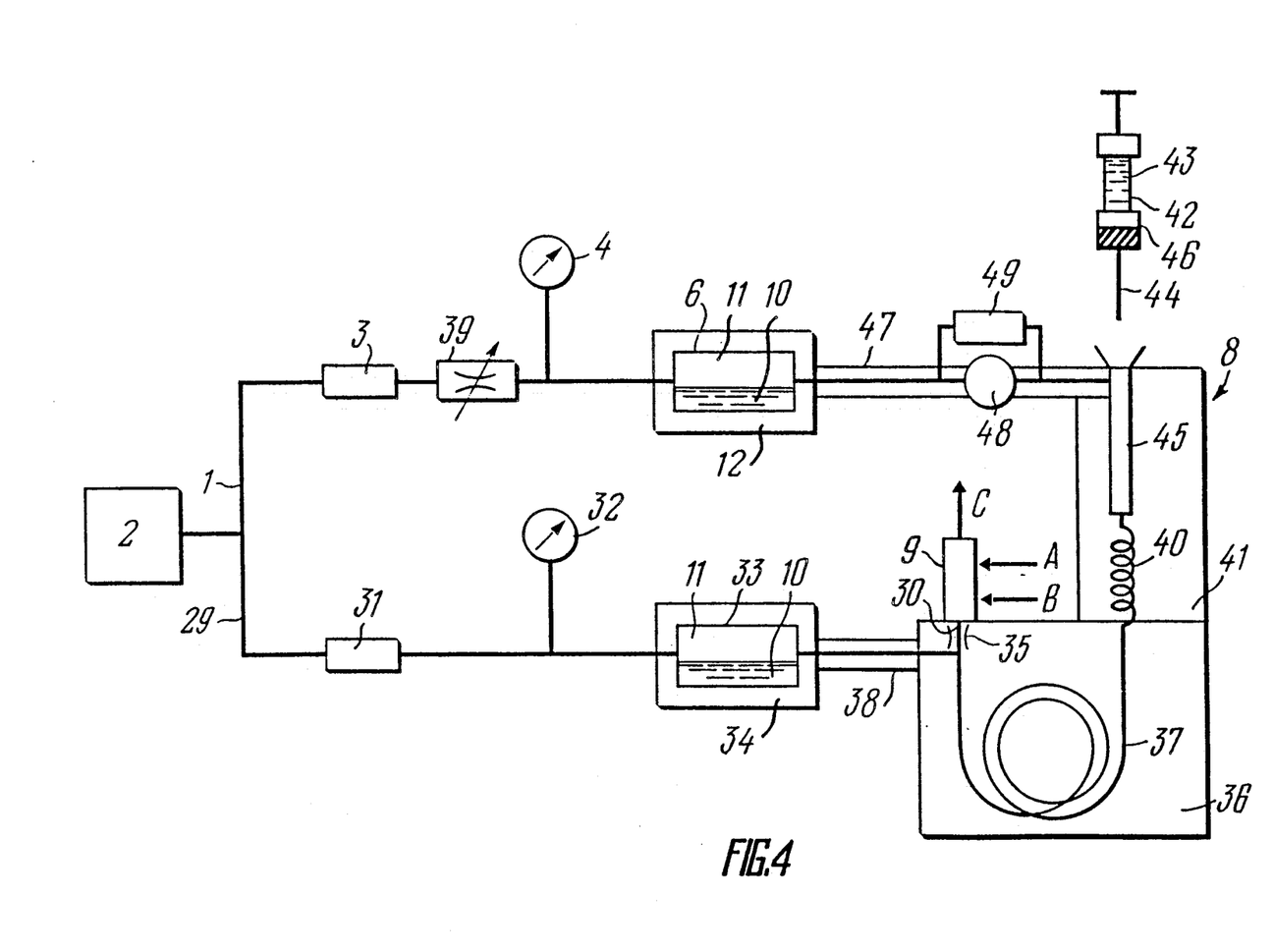
FIG. 4 is the schematic diagram of one more embodiment of the proposed device for carrying out the method according to the invention, wherein a sample of a mixture to be analyzed mixture is directly fed to the chromatograph column.

Turning now to FIG. 4 there is shown another embodiment of the device for carrying out the proposed method, which is essentially similar to the device of FIG. 1.

The sole difference is that the device of FIG. 4 comprises still another pipe-line 29 connecting the carrier-gas source 2 to an input 30 of the detector 9. Also, the illustrated embodiment of the device includes the following components successively arranged on the pipe-line 29: a carrier-gas pressure regulator 31 with a pressure indicator 32 placed at its output and a saturator 33 partially filled with the liquid solvent 10. The saturator 33 is essentially similar to the carbonator 6. It is placed in an individual thermostat 34 to maintain a predetermined temperature in saturating the carrier gas with vapors of the solvent 10.

A fixed pneumatic resistor 35, for example, a restrictor is placed at the input 30 of the detector 9 after the point of its connection with the pipe-line 29.

A heater 38 is used to heat the section of the pipe-line 29 between the thermostat 34 and a thermostat 36 accommodating a chromatograph column 37 which is a hollow capillary tube. The output of the chromatograph column 37 is connected to the pipe-line 29 at the point of its connection with the input 30 of the detector 9.

In the illustrated embodiment of the device for carrying out the proposed method, a variable pneumatic resistor 39, for example, a needle valve is placed on the pipe-line 1 between the carrier-gas pressure regulator 3 and the thermostat 12 so that the pressure indicator 4 is found at the output of the pneumatic resistor 39.

In the preferred embodiment of the device, the means 8 for introducing samples of a mixture to be analyzed comprises a liquid-sample evaporator formed with a capillary tube 40 enclosed in an individual thermostat 41 to maintain a temperature equal to the analyzed-mixture evaporating point and a microsyringe 42 filled with a liquid sample 43 of a mixture to be analyzed, which is supplied by a needle 44 to an input section 45 of the capillary tube 40. The needle 44 is inserted in the microsyringe 42 by the use of a sealing gasket 46. The output of the capillary tube 40 is connected to the input of the chromatograph column 37 which is a hollow capillary tube.

Arranged in the section of the pipe-line 1 between the thermostat 12 and the thermostat 41 heated by a heater 47 is a control valve 48, say a solenoid-operated valve opening or shutting off the pipe-line 1 in said section. Placed in parallel with the valve 48 is a pneumatic resistor 49 used to vent a portion of the carrier gas when said section of the pipe-line 1 is shut off by the valve 48.

The device for gas-chromatographic analysis of mixtures to accomplish the proposed method operates in the following manner.

Referring to FIG. 1 the saturator 6 for saturating the carrier gas with vapors of the solvent 10 is partially filled with said solvent which is a volatile liquid, for example, distilled water and placed in the thermostat 12. This is done by connecting the input and the output of the saturator 6, respectively, to the output of the capillary tube 5 for heating the carrier gas and to the heated section of the pipe-line 1. The temperature set in the thermostat 12 is equal to the saturation point (40° to 80° C. for water). Simultaneously, predetermined temperatures are set for the sample introduction means 8, the thermostat 14 and the detector 9 to prevent concentration of vapors of the volatile liquid inside said assemblies of the proposed device and within the heated section of the pipe-line 1.

The subsequent steps involve passing a given carrier-gas flow through the pipe-line 1, setting a desired pressure at the input of the saturator 6 with the pressure regulator 3 and noting the pressure value by reference to the pressure indicator 4. The input pressure of the carbonator 6 should be adjusted so that the carrier-gas flow through the chromatograph column 7 representing a capillary tube is in the range from 0.5 to 10.0 ml/min depending on the diameter of the capillary tube.

The carrier-gas flow passing through the saturator 6 for saturating the carrier gas with vapors of the volatile liquid is saturated to an equilibrium whereupon it is supplied through the pipe-line 1 and the sample introduction means 8 to the chromatograph column 7 representing a capillary tube and then to the detector 9. The vapors of the volatile liquid are adsorbed on the inner walls of the column 7 representing a capillary tube, thereby forming a uniform layer of adsorbed molecules of the volatile liquid on the column walls, said layer being the stationary liquid phase. The sample is introduced into the flow of the gas-vapor moving phase supplied through the sample introduction means 8 to the column 7 representing a capillary tube wherein the components of the analyzed mixture are chromatographically separated due to a difference in distribution of these components between the gas-vapor moving phase and the adsorbed layer of molecules of said volatile liquid. The separated components of the analyzed mixture are detected at the output of the column 7 which is a capillary tube by means of the detector 9.

The operation of the device of FIG. 2 is essentially similar to the operation of the device shown in FIG. 1.

The difference is that the measured amount of the liquid (fractions of a microliter) taken from the flow by the use of the metering device 15 (FIG. 2) of the sample introduction means 8 is supplied as a piston by the gas-vapor moving phase fed from the output of the saturator 6 into the capillary tube 16 whose temperature is maintained above the evaporation point of the mixture to be analyzed. The measured amount of the liquid sample, length of the capillary tube 16, its temperature and speed of the gas-vapour moving phase supplied thereto are chosen so that, while a specified amount of the analyzed liquid passes through the capillary tube 16, said liquid is completely evaporated. The formed vapour acting as a piston is transferred to the chromatographic column 7 representing a capillary tube wherein the chromatographic separation occurs.

The device of FIG. 3 operates in much the same manner as the device of FIG. 1.

The difference in operation is that the carrier-gas flow is saturated with solvent vapors at the same temperature as in chromatographic separation of the analyzed mixture in the chromatograph column 23 (FIG. 3) which is a capillary tube. The saturation conditions should prevent condensation of solvent vapours on the inner walls of the column 23 but allow their adsorption.

In this case a sample of to be analyzed liquid mixture is introduced by means of the evaporator 25 by partitioning the flow so that a greater part of the sample is vented to atmosphere with the gas-vapour moving phase through the pipe-line 27 by way of the pneumatic resistor 26, which is done to provide an optimal load for the column 23 which is a capillary tube.

The device of FIG. 4 operates in much the same manner as the device of FIG. 1.

The difference in operation is that the valve 48 (FIG. 4) is shut off at the instant preceding introduction of the sample. The principal carrier-gas flow is supplied along the pipe-line 29 through the pressure regulator 31 and the carbonator 33 by way of the heated section of the pipe-line 29 to the input of the detector 9 via the pneumatic resistor 35. Thereafter the carrier-gas flow saturated by solvent vapours in the saturator 33 is split. A portion of the flow is fed through the pneumatic resistor 35 to the detector 9 and then vented to atmosphere. Optimal operating conditions are, thus, created in the detector 9. The other portion of the flow comes to the output of the chromatograph column 37 representing a capillary tube. It passes through said column from the output to the input and is vented to atmosphere through the capillary tube 40 and its input section 45.

Passed through the pipe-line 1 at the instant preceding sample introduction is also a small part of the carrier-gas flow (0.5 to 1 ml/min), which is saturated by solvent vapours in the carbonator 6 and fed via the heated section of the pipe-line 1 and the pneumonic resistor 49 to the sample introduction means 8 whereupon it is also vented to atmosphere.

At the moment the liquid sample is introduced, the microsyringe 42 is used to obtain a measured amount of the liquid for analysis 43. Then the needle 44 of the microsyringe 42 is inserted in the input section 45 of the capillary tube 40 of the sample introduction means 8 and the cavity of the input section 45 of the tube 40 is hermetically sealed with the gasket 46. At this time, the control valve 48 is automatically opened and the preset carrier-gas flow saturated with solvent vapors is fed to the sample introduction means 8. The liquid sample 43 is slowly introduced into the sample introduction means 8 and then transferred by the gas-vapor moving phase to the capillary tube 40 wherein it passes off in vapor. The formed vapor piston is transferred by the gas-vapor moving phase to the column 37 representing a capillary tube, in which the mixture is chromatographically separated.

The separated components of the analyzed mixture are transferred by the combined gas-vapor flow, made up of the gas-vapor moving phase derived from the column 37 representing a capillary tube and the gas-vapor moving phase transmitted through the heated section of the pipe-line 29, via the pneumatic resistor 35 to the detector 9 wherein they are detected. It should be stressed that, while the components of the analyzed mixture are separated and detected, the input section 45 of the tube 40 of the sample introduction means 8 must be hermetically sealed with the gasket 46 of the microsyringe 42. After the detector 9 receives all the components of the mixture to be analyzed, the input section 45 is unsealed by removing the needle 44 of the microsyringe 42 from said input section 45 of the tube 40 of the sample introduction means 8 and the valve 48 is shut off simultaneously.

The gas system of the proposed device is then returned to the initial state preceding sample introduction, wherein the flow comprising the gas-vapor moving phase coming to the output of the chromatograph column 37 representing a capillary tube blows it in the opposite direction to vent the remaining mixture to atmosphere.

Given below are examples illustrating the use of the proposed method and the device therefor in making a chromatographic analysis.

EXAMPLE 1

Analyses were made by the use of the device of FIG. 3 for carrying out the proposed method.

In this device, the chromatographic column 23 was a hollow capillary tube of stainless steel having an inner diameter of 0.47 mm and a length of 6.5 mm.

The carrier gas was pure helium supplied from a bottle. The space velocity of the carrier gas was 0.6 ml/min through said hollow capillary tube and 60 ml/min through the discharge pipe-line 27, that is, the division ratio of the flow and, thus, of the sample at the input of the column 23 (capillary tube) was 1:100. The temperature of the column 23 (capillary tube) was maintained at 70° C., that is, below the boiling point of solvent (distilled water). The temperature of the evaporator 25 was 150° C. and the temperature of the detector 9 was 140° C.

The thermostat 24 accommodated both the chromatograph column 23 and the saturator 22 made as a cylindrical vessel partially filled with the liquid solvent 10 (distilled water), through the layer of which the carrier-gas flow had been bubbled before its arrival at the evaporator 25. The temperature in saturating the carrier gas with water vapors was 70° C., a factor preventing condensation of water vapors on the inner surface of the column 23 (capillary tube).

Subjected to analysis was a mixture of normal spirits $C_1-C_5$ (methanol, ethanol, propanol, butanol, pentanol—peaks 50, 51, 52, 53, 54, respectively), which was introduced into the evaporator 25 in the amount of 0.1 $\mu l$.

Figure 5:
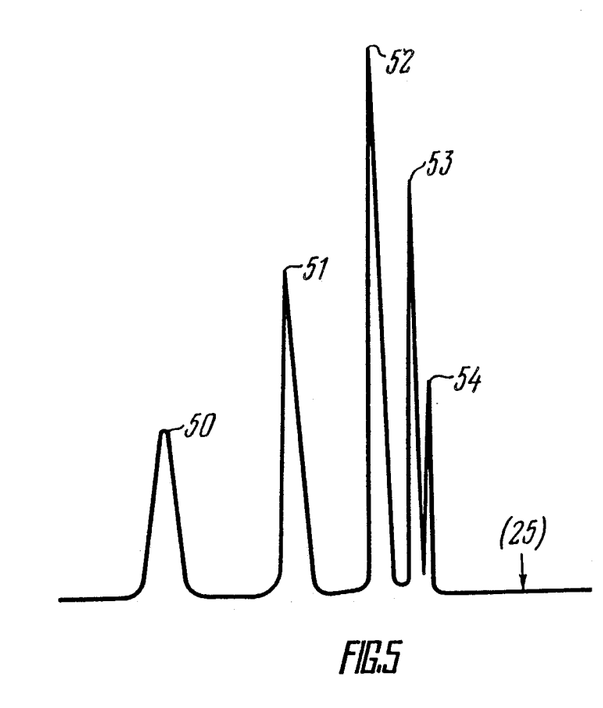
FIG. 5 is a chromatogram depicting separation of a mixture of normal spirits $C_1-C_5$, which was obtained by the device of FIG. 3.

FIG. 5 is a chromatogram depicting separation of a sample of a mixture of normal spirits $C_1-C_5$.

Referring to the chromatogram it is apparent that the degree of solubility of the analyzed substances in water determines the order of their output. The first peak 54 corresponds to the heaviest alcohol (pentanol) which is the least soluble component of all the spirits analyzed. Conversely, the last peak 50 corresponds to methanol which is the most soluble component.

Figure 6:
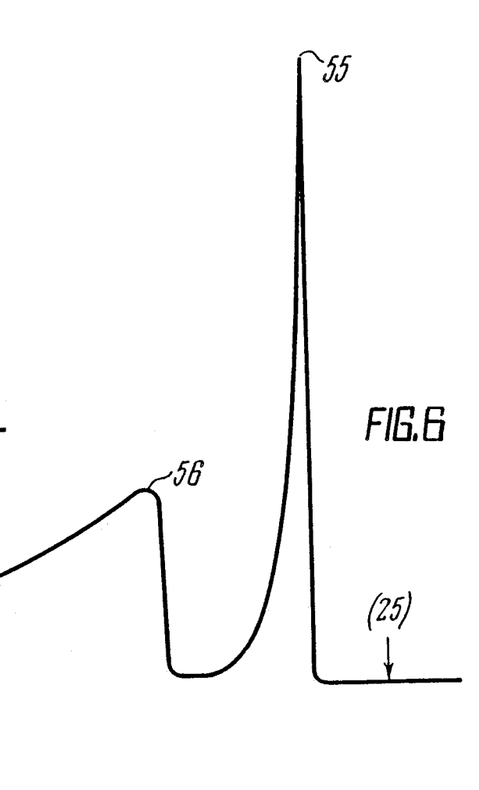
FIG. 6 is a chromatogram depicting separation of a binary mixture of normal spirits $C_1$ and $C_4$, which was obtained by the device of FIG. 3.

For comparison, FIG. 6 shows a chromatogram illustrating separation of a binary mixture of normal spirits $C_1$ and $C_4$ (0.5 $\mu l$ of the methanol-butanol mixture). Said chromatogram was obtained under the same conditions (including the temperature and speed of the carrier gas flowing through the hollow capillary tube), except for the fact that a pure carrier gas (helium) unsaturated with water vapors was passed through the capillary tube.

Referring to the chromatogram it is apparent that the components of the analyzed mixture were completely separated due to the adsorption interaction between vapors of the analyzed substances and the inner surface of the capillary tube of stainless steel. The order in which the components of the mixture are transferred from the capillary tube to the detector 9 is directly dependent upon their boiling points. The first peak 55 corresponds to methanol which has a lower boiling temperature as compared with butanol (second peak 56). Clearly seen in the chromatogram are "tails" of peaks characterizing the separated components, which are typical of polar compounds separated by the use of adsorbents.

EXAMPLE 2

The analysis conditions and the device were essentially similar to those described in Example 1.

The difference consisted in that the carbonator 6 (FIG. 1) was placed in its own thermostat 12 wherein the temperature was kept at 90° C., that is, above the temperature of the column 7 (t=70° C.).

Thus, appropriate conditions were provided to enable condensation of vapor of distilled water in the column 7 (hollow capillary tube) from the gas-vapor flow supplied from the carbonator 6 through the sample introduction means 8.

Subject to analysis was a mixture of normal spirits $C_1-C_5$, which was introduced into the means 8 in the amount of 0.1 $\mu l$.

Figures 7, 8:
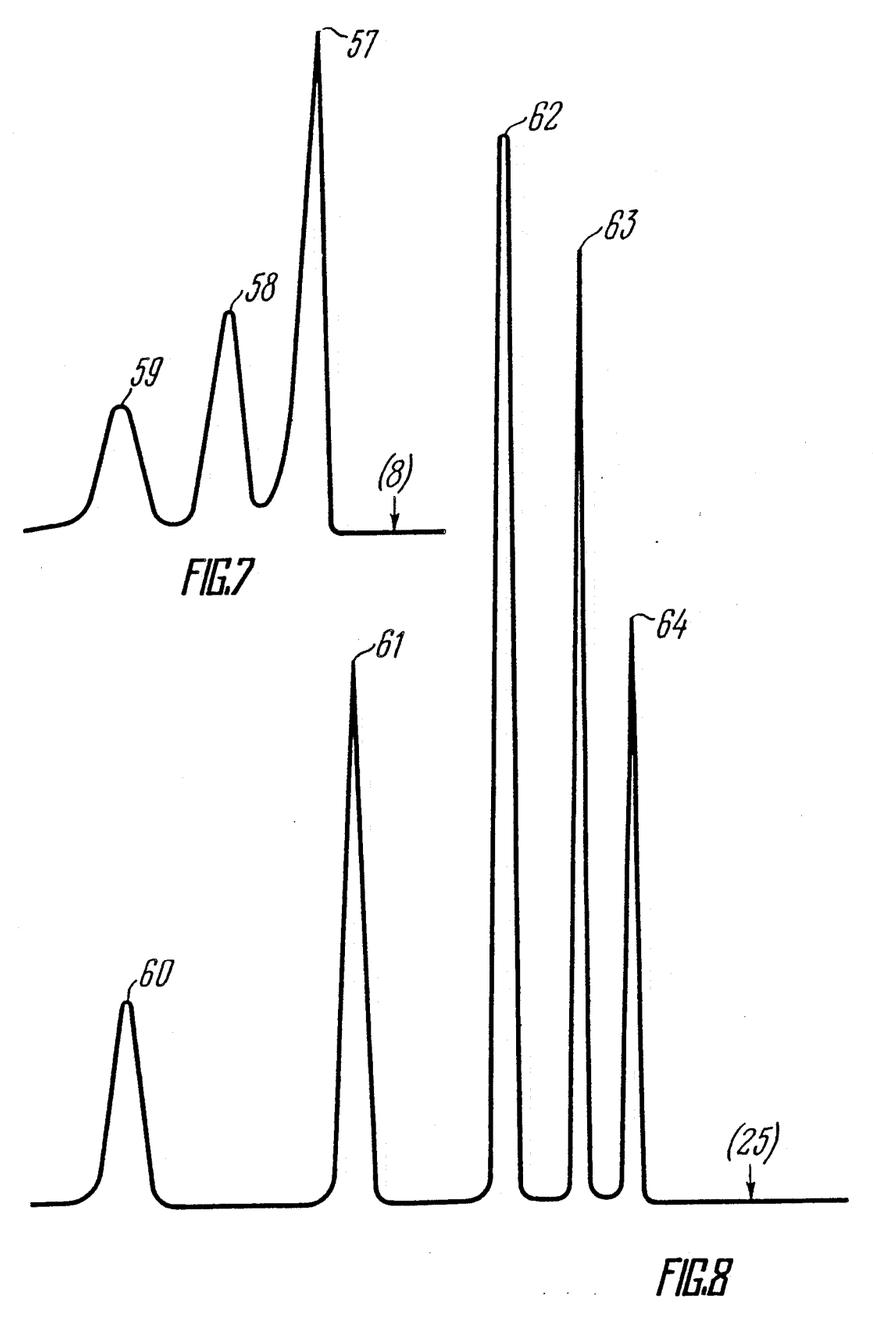
FIG. 7 is a chromatogram showing separation of a mixture of normal spirits $C_1-C_5$, which was obtained by the device of FIG. 1 under conditions characterized by condensation of solvent vapors in the chromatograph column according to the invention.
FIG. 8 is a chromatogram showing separation of a mixture of normal spirits $C_1-C_5$, which was obtained by the device of FIG. 3 after introducing an additional amount of distilled water into the chromatograph column.

FIG. 7 is a chromatogram showing separation of a sample of normal spirits $C_1-C_5$. The chromatogram was obtained under the specified analysis conditions.

Referring to the chromatogram it is seen that, with the analysis involving the use of the column 7 (hollow capillary tube) in conditions of condensation of water vapors on the inner surface of the tube, effectiveness and separation with the results obtained in making the analysis in conditions excluding condensation of solvent vapors in the column 7. More specifically, heavy spirits (pentanol, butanol and propanol) are not practically separated under the above conditions, due to which the first peak 57 is a common one. The subsequent peaks 58 and 59 correspond to ethanol and methanol, respectively.

Moreover, in operation with condensation of some of solvent vapors on the inner surface of the hollow capillary tube, there occurred a steady change in separation conditions due to growth of the condensed solvent layer in the column up to "flooding" conditions when the column (capillary tube) is filled to capacity with solvent.

EXAMPLE 3

The analysis conditions and the device used were essentially the same as in Example 1.

As distinct from Example 1, the saturator 6 (FIG. 1) was placed in its own thermostat 12 wherein the temperature was maintained at 30° C., that is, below the temperature of the chromatographic column 7 (t=70° C.).

Thus, the analysis conditions prevented condensation of solvent vapors in the column 7. A mixture of normal spirits $C_1$–$C_5$ was analyzed after attaining equilibrium characterized by constant holding times for components of the analyzed mixture (methanol and butanol).

The obtained chromatogram fully conformed to the chromatogram of FIG. 5 obtained under the analysis conditions of Example 1.

EXAMPLE 4

The analysis conditions and the device used were similar to those utilized in Example 1.

Subjected to separation was a mixture of normal spirits $C_1$–$C_5$. 100 μl of distilled water were additionally introduced into the evaporator 25 after reaching equilibrium in the chromatograph column 23 (FIG. 3), which is characterized by a constant time at which the separated substances come out of the column 23. A larger portion of water vapor was vented to atmosphere through the pipe-line 27, while a smaller portion thereof (about 1 μl) was supplied to the chromatograph column 23, thus forming on its inner surface an additional water layer serving as the stationary liquid phase. Thereupon the analyzed mixture of normal spirits $C_1$–$C_5$ was introduced into the evaporator 25.

FIG. 8 is a chromatogram illustrating separation of said mixture of normal spirits $C_1$–$C_5$ (methanol, ethanol, propanol, butanol, pentanol—peaks 60, 61, 62, 63, 64, respectively).

Comparing the chromatograms of FIGS. 5 and 8 showing separation of the same mixture it is apparent that the separation capacity of the chromatographic column 23 sharply increased after a measured amount of solvent was added thereto (FIG. 8).

EXAMPLE 5

It was proved that a direct relationship exists between the holding time for components of the separated mixture and the solvent (distilled water) content of the column 23 (FIG. 3). As the solvent content of the column 23 increases, the height equivalent of the theoretical plate and characterizing separation efficiency is decreased.

Figure 9:
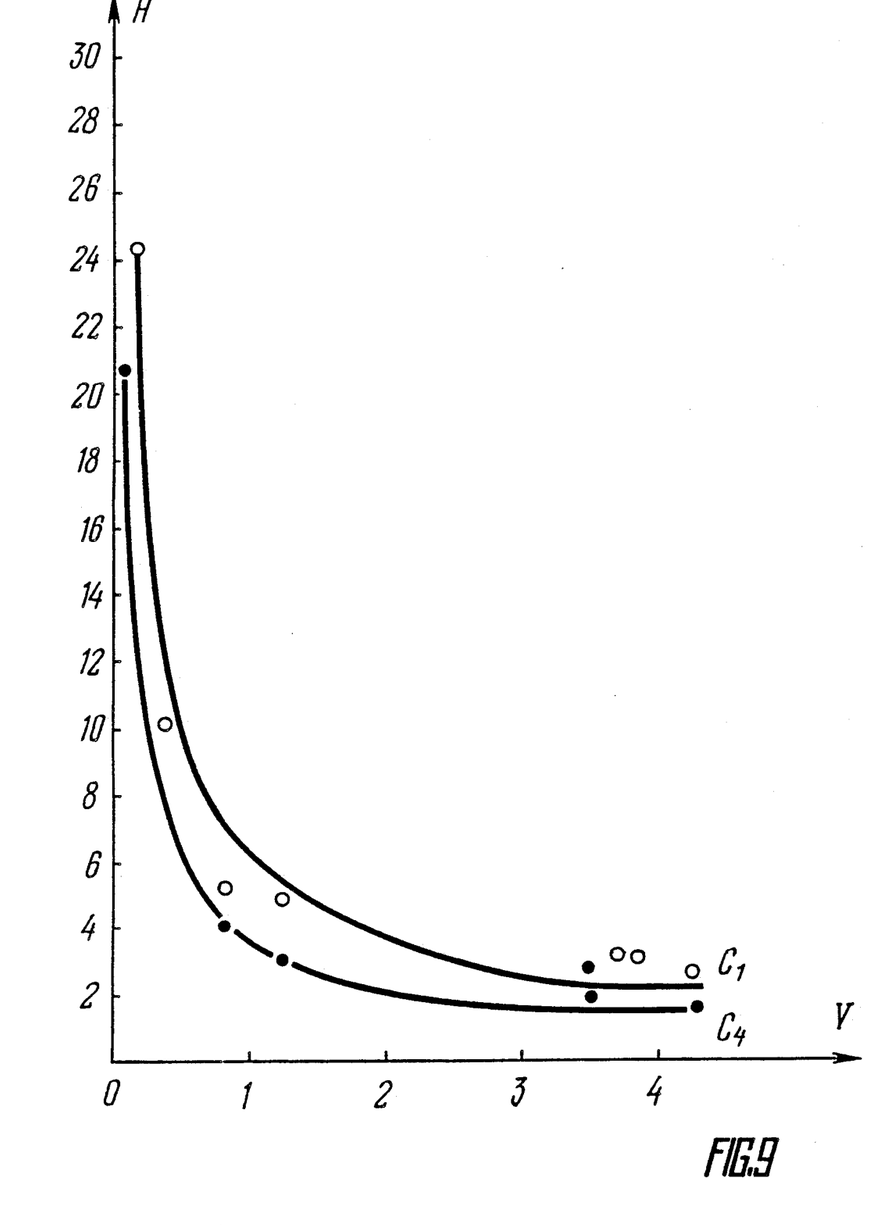
FIG. 9 shows the relationship between heights equivalent of a theoretical plate for normal spirits $C_1$ and $C_4$ and the amount of distilled water in the chromatograph column in the device of FIG. 3 after repeated supplies thereof to said column.

FIG. 9 shows dependence of the height equivalent of the theoretical plate for normal spirits $C_1$ and $C_4$ (methanol and butanol) on the distilled-water content of the column 23. Plotted on the abscissa is the quantity of solvent in the column 23 (V, μl), whereas the height equivalent of the theoretical plate (H, mm) is laid off as ordinate. Referring to FIG. 9 it is seen that effectiveness of the column 23 increases with the water content therein.

Consequently, in the proposed method the separation capacity of the column 23 may be changed as desired (by ten or more times) by making controlled changes in the solvent content of the column 23.

EXAMPLE 6

The analysis conditions and the device were similar to those used in Example 1.

Subjected to separation was a mixture comprising normal spirits $C_1$, $C_3$ and $C_4$ (methanol, propanol and butanol) and aromatic hydrocarbons (benzene and toluene).

Before introducing the analyzed mixture, the evaporator 25 was fed with a measured amount (100 μl) of solvent (distilled water) to increase the separation capacity of the chromatograph column 23. Thereupon the mixture to be analyzed was introduced into the evaporator 25 in the amount of 0.1 μl.

Figure 10:
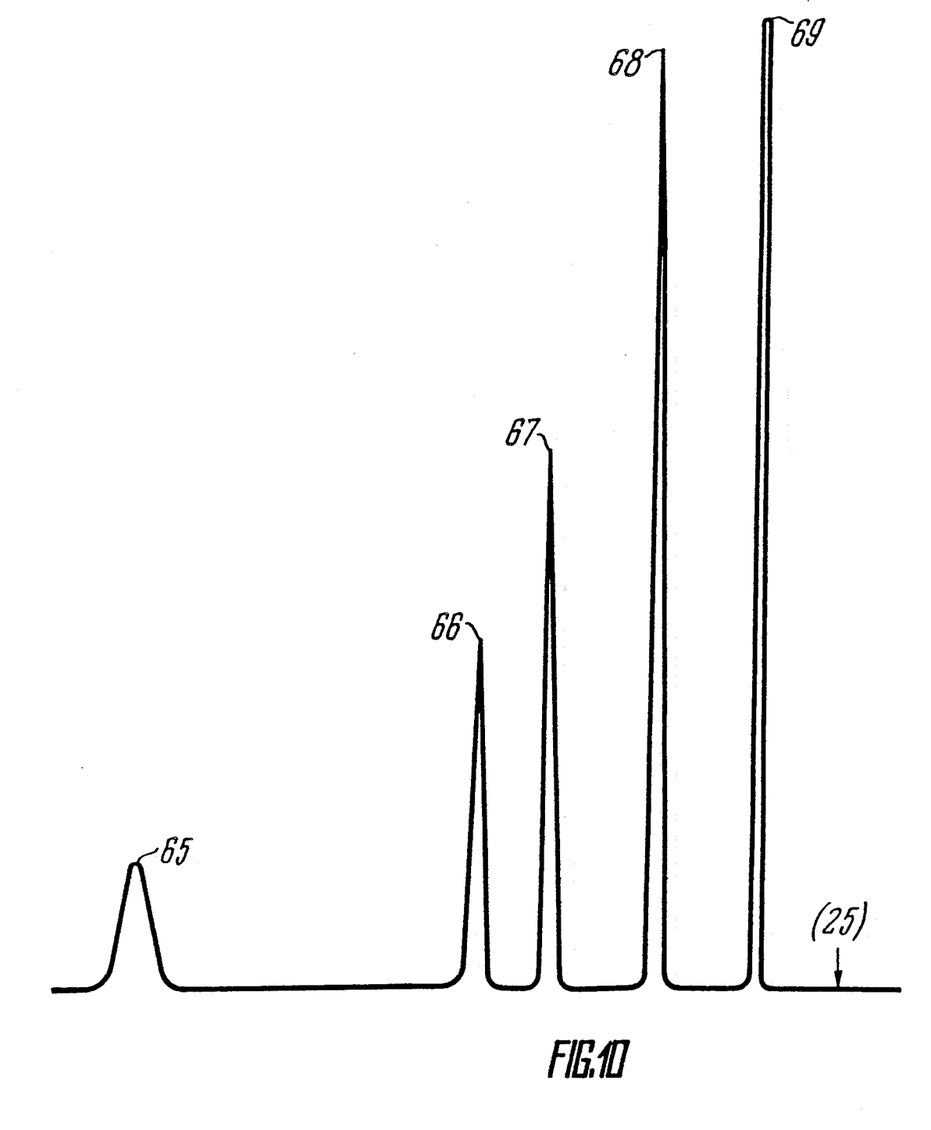
FIG. 10 is a chromatogram showing separation of a mixture of normal spirits $C_1$, $C_3$ and $C_4$ and aromatic hydrocarbons, which was obtained by the device of FIG. 3.

Referring to the chromatogram of FIG. 10 it is apparent that, under the specified conditions, the analyzed mixture (methanol, propanol, butanol, benzene, toluene—peaks 65, 66, 67, 68, 69, respectively) was completely separated. The order in which the output of said components occurred was determined by their solubility in water. The least soluble benzene (peak 68) and toluene (peak 69) came out earlier than the more soluble spirits (peaks 67, 66, 65).

Hence, the proposed method accomplished by the device in compliance with the invention permits a gas-chromatographic analysis of mixtures, wherein solvent vapors adsorbed on the inner surface of the chromatograph column (hollow capillary tube) are used as separation material in said column. Selectivity and separation capacity of the chromatograph column may be changed without its replacement, more particularly, by changing the type of solvent and adding a measured amount of solvent to the column, a feature making the proposed method suitable for use with highly efficient capillary chromatographic slot columns obtained by etching rectangular channels in silicon plates and having the efficiency over 100 thousand theoretical plates per meter.

The proposed method accomplished by the device according to the invention makes it possible to increase effectiveness and separation capacity of the chromatograph column and also separation stability with time by stabilizing the amount of solvent in the column with time.

Similarly to the widely known method of capillary gas chromatography with capillary columns having their inner surface covered with a layer of the stationary liquid phase, the proposed method increases the service life of the column due to continuing restoration of a layer of solvent molecules adsorbed on the inner surface of the capillary column. The capillary column used in the device for carrying out the proposed method may operate without any change in its separation capacity practically beyond bounds, whereas conventional capillary chromatograph columns used in the known methods of capillary gas chromatography lose their effectiveness after a fairly short time period (6 to 10 months of continuous operation).

Specific narrow terms have been used for clarity in the description of the preferred embodiments of the invention. However, the invention is not limited to the exact terms used for it is understood that each such term embraces all equivalent terms functioning similarly and used for solving the same problems.

While particular embodiments of the invention have been shown and described, various modifications thereof will be apparent to those skilled in the art and therefore it is not intended that the invention be limited to the disclosed embodiments or to the details thereof and the departures may be made therefrom within the spirit and scope of the invention as defined in the claims.

What is claimed is:

1. A method of gas-chromatographic analysis of mixtures comprising:

using as a chromatograph column a hollow capillary tube which continuously passes a carrier-gas flow saturated with solvent vapors at a temperature below or equal to the temperature of said chromatograph column maintained above the condensation point of vapors of said solvent and below the boiling point of said solvent;

periodically introducing a sample of mixture to be analyzed into said chromatograph column after attaining the equality between the quantity of vapors of said solvent supplied to said chromatograph column and the quantity of vapors of said solvent removed from said chromatograph column; and subsequently detecting at the output of said column components of said mixture separated in said chromatograph column.

2. A method as claimed in claim 1, wherein:

said equality between the quantity of vapors of said solvent supplied to said chromatograph column and the quantity of vapors of said solvent removed from said chromatograph column is determined by additionally introducing a sample of a mixture into said chromatograph column and noting the moment at which the output of components of said mixture from said chromatograph column is stabilized.

3. A method as claimed in claim 1, wherein:

before said periodic introduction of a sample of said mixture to be analyzed into said chromatograph column, said column is additionally supplied with a measured amount of vapors of said solvent.

4. A method as claimed in claim 3, wherein:

said additional introduction of said measured amount of vapors of said solvent into said chromatograph column is repeated many times until a desired degree of separation of components of said analyzed mixture is obtained.

5. A device for gas-chromatographic analysis of mixtures, comprising:

such series-connected components as a carrier-gas source;

a means for supplying solvent vapors to the flow of said carrier gas, which comprises a first saturator partially filled with liquid solvent;

a means for introducing samples of a mixture to be analyzed into said carrier-gas flow saturated with vapors of said solvent; and a chromatograph column representing a hollow capillary tube, having an input and an output and receiving at said input said sample of the analyzed mixture from the carrier-gas flow saturated with vapors of said solvent;

a first pipe-line used to effect said series connection;

a first thermostat accommodating said first carbonator and used to maintain a predetermined temperature in saturating said carrier gas with vapors of said solvent;

second thermostat containing said chromatograph column and designed to maintain a predetermined temperature in separating components of said analyzed mixture in said chromatograph column; and a detector having an input connected to said output of said chromatograph column via said first pipe-line and detecting components of said analyzed mixture separated in said chromatograph column.

6. A device as claimed in claim 5, wherein said first thermostat of said first saturator and said second thermostat of said chromatograph column are made integral, thus forming a common thermostat.

7. A device as claimed in claim 5, comprising:

a second pipe-line connecting said carrier-gas source to said input of said detector and to said output of said column; and such successively arranged components on said second pipe-line as a carrier-gas pressure regulator;

a second saturator partially filled with said liquid solvent and placed in its thermostat to maintain a predetermined temperature in saturating said carrier gas with vapors of said solvent; and a fixed pneumatic resistor placed at said input of said detector after the point of connection of said second pipe-line with said input of said detector and with said output of said chromatograph column.

* * * * *